United States Patent
Murakami et al.

(10) Patent No.: US 8,430,896 B2
(45) Date of Patent: Apr. 30, 2013

(54) SURGICAL APPLIANCE FOR USE IN TAKING OUT TRANSPLANT-USE TENDON AND IN REGENERATING OPERATION OF TENDON AT LOCATION WHERE TRANSPLANT TENDON WAS TAKEN OUT

(75) Inventors: Hidetaka Murakami, Kurume (JP); Takashi Soejima, Kurume (JP); Hideki Yasunaga, Kurume (JP)

(73) Assignee: Kurume University, Kureme-shi (JP)

( * ) Notice: Subject to any disclaimer, the term of this patent is extended or adjusted under 35 U.S.C. 154(b) by 783 days.

(21) Appl. No.: 12/525,288

(22) PCT Filed: Jan. 30, 2008

(86) PCT No.: PCT/JP2008/051442
§ 371 (c)(1),
(2), (4) Date: Jul. 30, 2009

(87) PCT Pub. No.: WO2008/093747
PCT Pub. Date: Aug. 7, 2008

(65) Prior Publication Data
US 2010/0069944 A1    Mar. 18, 2010

(30) Foreign Application Priority Data
Jan. 31, 2007    (JP) ................................ 2007-022121

(51) Int. Cl.
*A61B 17/32*    (2006.01)
(52) U.S. Cl.
USPC ......................................... 606/167; 600/566

(58) Field of Classification Search .................... 606/79, 606/167, 170, 171, 184; 600/566, 567
See application file for complete search history.

(56) References Cited

U.S. PATENT DOCUMENTS

| 4,773,417 A | 9/1988 | Moore et al. |
| 4,901,717 A | 2/1990 | Moore et al. |
| 5,911,730 A | 6/1999 | McGuire |
| 6,217,599 B1 | 4/2001 | McGuire |
| 2005/0124914 A1* | 6/2005 | Dicarlo et al. ................ 600/567 |

FOREIGN PATENT DOCUMENTS
JP    02-503999 A    11/1990

OTHER PUBLICATIONS

A Product Catalogue _A Surgical Appliance for Reconstruction of ACLPCL Implant May 2006—1 p. 9 by Smith and Nephew Inc Endoscopy Division .pdf.

* cited by examiner

*Primary Examiner* — Victor Nguyen

(57) ABSTRACT

A surgical appliance for taking out a transplant-use tendon in surgery and assisting reconstruction of the tendon after take out. The surgical appliance has a tendon cutter, guide tube, a grip portion and a guide needle. The guide tube is a hollow thin tube having open opposing ends, wherein a distal end opening constitutes a discharger port of the guide needle. A through hole is formed in the grip portion in the direction of a central axis, and the proximal end side outlet of the through hole constitutes an insertion port. The guide needle is provided with a sharp conical tip on a distal end side and a threading hole on a proximal end. The guide needle is inserted into the guide tube, such that the opposite ends may be exposed from the discharge port and the insertion port when it is inserted into the guide tube.

3 Claims, 5 Drawing Sheets

SURGICAL APPLIANCE FOR USE IN TAKING OUT TRANSPLANT-USE TENDON AND IN REGENERATING OPERATION OF TENDON AT LOCATION WHERE TRANSPLANT TENDON WAS TAKEN OUT

CROSS-REFERENCE TO RELATED APPLICATIONS

This is a U.S. national phase application under 35 U.S.C. §371 of International Patent Application No. PCT/JP2008/051442 filed Jan. 30, 2008 and claims the benefit of Japanese Application No. 2007-022121 filed Jan. 31, 2007. The International Application was published in the Japanese language on Aug. 7, 2008 as International Publication No. WO/2008/093747 under PCT Article 21(2). The contents of these applications are incorporated by reference herein in their entireties.

FIELD OF THE INVENTION

The present invention relates to a surgical appliance used by being inserted into the inside of a living body, such as human, to be operated on. More specifically, the present invention relates to a surgical appliance for use in removing a transplant-use tendon and regenerating the tendon after removal.

BACKGROUND OF THE INVENTION

Transplanting a tendon for replacing a ruptured ligament by surgery is one of the conventional methods for curing a broken ligament due to an injury or damage caused by an accident.

Especially, an anterior cruciate ligament (hereinafter referred to as "ACL") rupture which frequently occurs in professional sports such as in baseball and soccer, also occurs at a high frequency among general public during exercise and due to accidents. The number of ruptures per year reported in Japan has been 20,000 to 30,000, and 100,000 in the United States. 15,000 cases in Japan and 50,000 to 75,000 cases in the United States received treatments using the aforementioned reconstructing method.

Options for obtaining tendons for the abovementioned method for ligament curing are autograft transplantation using autogeneous tendons, which is predominantly performed; allograft transplantation using allogeneous tendons including tendons from dead body; and artificial graft reconstruction.

In an autograft transplantation, transplant-use tendons are usually supplied from one of the patellar ligament (a tendon at the front side of patella), the semitendinosus ligament (and gracilis ligament), iliotibial band (a ligament at the side of thigh) and the quadriceps femoris tendon. In many cases, the patellar ligament or semitendinosus tendon (and gracilis tendon) is used.

The supplied ligaments described above are used for surgical reconstruction of a ruptured ACL. In the single-socket method, for example, a tunnel is formed from the lower part of the femur to the upper part of the cnemis, through which a ligament is directed to be used as a replacement of ACL.

Using the abovementioned single-socket method, there are two types of surgical procedures to perform an autograft tendon reconstruction. One method uses a patellar ligament, more specifically, a tendon under the patella is taken out and transplanted to the position of the ACL (hereinafter referred to as the "BTB method"). Another method uses a semitendinosus tendon, to be more precise, a string-shaped tendon located at rearward of inner side of knee is taken out and folded four times in order to increase its thickness, and this tendon is transplanted to the position of ACL (hereinafter referred to as the "ST method").

However, the BTB method has problems as follows:
(1) Pain may remain after surgery in the front side of the knee from which tendons and bones are taken out. (This is especially common in women.)
(2) Post-surgical algia/pain is more severe than when other methods are performed.
(3) Knee extension strength (kicking force) is weakened.
(4) The reconstructed tendon becomes flat.

In contrast, the ST method has several advantages as follows:
(1) There are two options, a "single-route practice" in which a single thick tendon is reconstructed, and a "double-route practice" in which two tendons are reconstructed.
(2) Post surgical pain is less at the site where the tendon is taken out.
(3) Surgical scarring is extremely small.
(4) Decrease in muscle strength after surgery is small.

For this reason, the instant inventor who engages in medicine has been performing surgeries in which semitendinosus tendons (and gracilis tendons) are taken out and transplanted. However, because such tendons are very long and thin, it is difficult to remove them.

SUMMARY OF THE INVENTION

An appliance for removing the aforementioned tendons is suggested in A Product Catalogue: A Surgical Appliance for Reconstruction of ACL/PCL & Implant, May 2006-1, p. 9 by Smith and Nephew Inc., Endoscopy Division, and this document is incorporated by reference herein. The appliance comprises a unit for cutting and separating tendon at the distal end of a rod, and the rod is inserted into a human body from the incision site, allowing an end side of the tendon to be cut and separated. The present inventor has used the appliance, because it was able to take out the tendon without a large incision and had an advantage of reducing the stress to a patient.

The present inventor has found that, during catamnestic observation of post-surgical patients after the aforementioned ST method was performed, the semitendinosus tendon (and gracilis tendon) were regenerated in many of the patients.

Such regeneration of said tendon after the tendon was surgically removed has also been reported from other researchers. The reason why the tendon regeneration occurs is yet to be identified, and remains as a matter of conjecture.

However, according to the findings from the present inventor and the reports from the other researchers as referred to above, regeneration of the semitendinosus tendon stopped before reaching to the area of the pes anserinus, to which it had been originally connected. Thus, the muscle strength with the regenerated tendon could not be sufficiently recovered to the level before the surgery.

Thus, the present inventor has developed a surgical procedure for use when surgically removing a semitendinosus tendon, in which one end of the residual tendon attached to the pes anserinus at the other end (such as a part of the gracilis/sartorius tendon or surrounding tendon tissues) is moved so that it runs in the same direction and position as the surgically removed semitendinosus tendon, and so serves as a guide tendon for regenerating the semitendinosus tendon.

Using the procedure described above, regeneration of the surgically removed semitendinosus tendon proceeds, guided by the moved residual tendon, and therefore attaches properly to the pes anserinus to which it (the semitendinosus tendon) was initially attached. Accordingly, when the semitendinosus tendon is regenerated, the strength of the regenerated tendon can be expected to recover to the pre-surgical level.

However, such a surgical operation of moving and surgically adjusting the position of the guide tendon so that it corresponds to the original direction of the semitendinosus tendon and placing it so that it properly guides the regenerating semitendinosus tendon to the pes anserinus is technically difficult.

After carrying out further research and development, the present inventor has developed a new appliance implemented by the present invention for assisting with the operation of aforementioned surgical procedure.

An object of the present invention is to provide a surgical appliance used for a procedure for taking out a transplant-use tendon by ablation or separation in surgery, and further, for allowing easy regeneration of a tendon at a desired site after taking out the tendon (also called "taking out a transplant-use tendon and assisting regeneration of the tendon after take out").

The present invention achieves the abovementioned objects are as follows:

The present invention may comprise a surgical appliance for taking out a transplant-use tendon and for assisting regeneration of the tendon after take out of the tendon, the surgical appliance being configured to be inserted into the inside of a living body to be operated on, including: a rod member having a predetermined length and unit to guide a needle-like member of the surgical appliance; a needle-like body guided by the rod member; wherein the rod member has a tendon cutting and separating unit at a distal end side thereof; and the needle-like member is provided with a skin breaking portion that is able to break the skin so that a threading hole is formed at the proximal end side thereof.

The present invention may comprise a surgical appliance for taking out a transplant-use tendon and for assisting regeneration of the tendon after take out of the tendon, the surgical appliance being configured to be inserted into the inside of a living body to be operated on, including: a tendon cutting and separating unit; a hollow tube having open opposing ends; and a needle-like body configured to be inserted in and to penetrate through the tube; wherein the tendon cutting and separating unit is provided at a distal end side of the tube; an opening at the distal end side of the tube constitutes a discharging port for inserting the needle-like body; an opening of the proximal end side thereof constitutes an inserting port for inserting the needle-like body; and a skin breaking portion that is able to break the skin is provided at the distal end of the needle-like body and a threading hole is formed at the proximal end side thereof.

The present invention may comprise a surgical appliance for taking out a transplant-use tendon and for assisting regeneration of the tendon after take out of the tendon, the surgical appliance being configured to be inserted into the inside of a living body to be operated on, including: a tendon cutting and separating unit; an axis body for controlling the tendon cutting and separating unit; and a hollow thin tube having open opposing ends; a needle-like body configured to be inserted in and to penetrate through the tube; and wherein, the tendon cutting and separating unit is provided at the distal end of the axis body; the tube is provided in a longitudinal direction of the axis body; an opening at the distal end side of the tube constitutes a discharging port of the needle-like body; an opening of the proximal side thereof constitutes an inserting port for inserting the needle-like body; and a skin breaking portion that is able to break the skin is provided at the distal end of the needle-like body and a threading hole is formed at the proximal end side thereof.

The present invention may comprise a surgical appliance for taking out a transplant-use tendon and for assisting regeneration of the tendon after take out of the tendon, the surgical appliance being configured to be inserted into the inside of a living body to be operated on, including: a tendon cutting and separating unit; an axis body for controlling the tendon separating unit that is formed with a guide groove; and a needle-like body that is formed so as to be able to be slid along the grooves of the axis body; and wherein the guide groove is provided at the whole or a part of the axis body in a longitudinal direction; the tendon cutting and separating unit is provided at an end side of the axis body; and a skin breaking portion that is able to break the skin is provided at the distal end of the needle-like body and a threading hole is formed at the proximal end side thereof.

The present invention may comprise a surgical appliance for taking out a transplant-use tendon and for assisting regeneration of the tendon after take out of the tendon, the surgical appliance being configured to be inserted into the inside of a living body to be operated on, including: a tendon cutting and separating unit including an open tube having open opposing ends; an axis body that is a hollow tube body having open opposite ends for controlling the tendon cutting and separating unit; and a needle-like body configured to be inserted in and to penetrate through the tube, wherein; the tendon cutting and separating unit is provided at an end side of the axis body; an opening at the distal end of the axis body constitutes a discharging port of the needle-like body; an opening at the proximal end side thereof constitutes an insertion port for inserting the needle-like body; a skin breaking portion that is able to break the skin is provided at the distal end of the needle-like body and a threading hole is formed at the base side thereof; and an attaching portion between the tendon cutting and separating unit and axis body is disposed that the needle-like body capable of passing through the axis body is discharged by being projected from the end side of the tendon cutting and separating unit.

The needle-like body of the present invention may be configured to have a length such that, when the needle-like body is in a state of being inserted into the tube body or mated with the guide groove, the end portion of the needle-like body is exposed from one or both openings of the tube body or from one or both ends of the guide groove.

The tendon cutting and separating unit of the present invention may be formed in a tube-shape and provided at an end side of the axis body so as to cut and separate a tendon by pressing a cutting blade formed at the distal side opening; or may be so formed that a plate material having a blade is coiled in a spiral shape with spaces therebetween to form a substantially cylindrical shape, so as to cut and separate a tendon by entangling it from the space between the spiral, and then by pressing or pulling the tendon.

Further, the present invention may be configured such that the tube body or axis body is provided with a grip portion at the proximal end side.

The rod member may be formed to have a tube body or axis body with a predetermined length which has a unit that guides a needle-like body by inserting into a living body. For example, the rod member may be a hollow tube body having open opposite ends so as to be able to guide a needle-like body, or may be an axis body formed with guide groove so as to guide the needle-like body, or may be a combination of a solid-core axis body and a hollow tube body having openings at the both ends and formed so as to able to guide a needle-like body.

"A living body to be operated on" includes not only humans but also animals such as horses, cattle and pigs.

The tendon cutting and separating unit may for example be formed in a tube shape having a cutting blade (211) at circle opening at the distal end side and formed so as to be able to cut and separate tendon by pressing (210, 410, 510). This type of tendon separating unit is called a "closed-type tendon cutter," hereinafter to be called the same (see FIG. 8), or may be formed in a substantial cylindrical shape by forming a plate material having a blade (111) to have a spiral shape with space so as to be able to cut and separate a tendon by tangling it from the space between the spiral and, further, pressing or pulling the tendon (110). This type of tendon separating unit is referred to as "open-type tendon cutter." (See FIG. 7) However, the tendon cutting and separating unit of the present invention is not limited to above-mentioned unit, and other known units, such as a small knife-like unit including scalpels or laser scalpel may also be used.

Further, the tube body may be configured to be unified with an axis body having a tendon cutting and separating unit at the distal end thereof. In this case in which the tendon cutting and separating unit is a cylindrical cutter which is the aforementioned open-type cutter or closed-type cutter, the needle-like body may be configured to pass through the tube body and the tendon cutting and separating unit. Likewise, in the aforementioned configuration in which the tube body has grooves, when the tendon cutting and separating unit has a cylindrical shape, the needle-like body can be configured to penetrate into the tendon cutting and separating unit having the configuration above.

A skin breaking portion may have a shape or configuration to be able to break the skin, for example, the distal end thereof may have a conical shape or a substantially conical shape such as a drill-like shape, or other known shapes such as a blade-like shape.

(Operation)

The operation of the surgical appliance for use in taking out a transplant-use tendon and regenerating work of the tendon after taking out relating to the present invention will be briefly explained. Note that the order of the operation regarding B and C may be reversed in the operation described below.

[A. Taking Out Tendons for Transplant-Use]

(1) Skin inside of a knee-joint is incised and a tendon to be taken out, which is selected from a semitendinosus tendon, gracilis tendon, or sartorius tendon, is cut and separated from the pes anserinus.

(2) First, before the operation, a needle-like body is removed from a surgical appliance for cutting and taking out a transplant-use tendon and assisting regenerating of the tendon after take out.

Next, a rod member including a tube body or an axis body of the surgical appliance for taking out transplant-use tendon and regenerating work of the tendon after take out, which hereinafter will be called as a rod member, is inserted from the incision and along the aforementioned tendon to be taken out. The tendon to be taken out is cut and separated by a tendon cutting and separating unit at the position at which the length of the tendon is enough to be transplanted.

In this operation, when the tendon cutting and separating unit is a closed-type cutter described above, an end portion of the tendon to be taken out which has been cut and separated from the pes anserinus is inserted from the distal end side opening of the cutter, the rod member is inserted along the tendon, and the cutter blade disposed at the distal end of the closed-type cutter is pressed against a portion where the length of the tendon is enough for transplant, to cut and separate a tendon to be taken out. When the cutter is an open-type cutter as described above, the end portion of a tendon to be taken out, which has been cut and separated from the pes anserinus, is inserted, a rod member is inserted along the tendon, and the cutter blade disposed at the distal end of the open-type cutter is pressed against a portion (where the length of tendon is enough for transplant) to cut and separate the tendon to be taken out. Alternatively, a rod member is inserted along the tendon and at a portion having a sufficient length for transplant, the tendon to be cut and separated is inserted in the space present between the spiral shape formed in the open-type cutter so that the tendon is entangled, and then the tendon to be cut is pressed or pulled by the open-type cutter to be cut and separated.

Then, the cut and separated tendon is taken out by pulling from the body and collected removed.

Note that, at this point, a rod member and other parts of the surgical appliance for use in taking out the transplant-use tendon and regenerating the tendon after taking out remains inside the body.

[B. Regeneration Work at the Site of a Transplant-Use Tendon has been Taken Out]

(3) A guide tendon is prepared. Specifically, among the tendons to be taken out described above, parts of the tendons other than the tendon that has been taken out are separated in a longitudinal direction at the tendon body between an origin of the tendon, which is at an inguinal region, and an insertion of the tendon, which is in the vicinity of pes anserinus, and pulled out from the incision.

(4) A needle-like body is inserted into a tube body from the inserting port of a rod member, or the needle-like body is inserted along grooves of an axis body, and the skin is penetrated with the skin breaking portion of the needle-like body at a level of the position where the taken out tendon is cut and separated (which is at an inner side of a vicinity where the taken outtendon is separated).

(5) A part of the needle-like body which is protruded from the skin is gripped and a rod member (and others) is pulled out from the body.

(6) A guide thread is put through a threading hole at the proximal end side of the needle-like body and the thread is looped. Note that the guide thread may be put through the threading hole and looped beforehand.

(7) The needle-like body is pulled out from the incision that was cut during procedure (4) above, at the distal end side of the needle-like body, and the guide thread is arranged corresponding to the direction and the position where the taken out tendon was presented. Thus, the guide thread for leading a guide tendon is able to be arranged in a direction of the tendon direction before the direction of the guide tendon is arranged, and set corresponding to the same direction and the position of the taken out tendon.

(8) The cut end of the guide tendon that has been pulled out is put into a loop of the guide thread in order to connect with the thread, and the thread with the guide tendon was pulled toward the proximal, a nearer side toward the body trunk. By this, the guide tendon is able to be arranged corresponding in a direction and a position of the taken out tendon so that an operation in which a guide tendon is guided to the pes anserinus by being moved corresponding to the direction and the position of a taken out tendon, and which was difficult in conventional surgical procedures, can be performed easily. Further, being guided by the transferred tendon, a tendon to be regenerated can be properly fixed to the pes anserinus which is a tendonious insertion prior to removal, and accordingly the possibility of the tendon regenerating becomes higher. With such proper tendon regeneration, the power of muscle with the tendon is expected to recover to the level before the surgery.

[C. Reconstruction of ACL]

(9) ACL reconstruction work is performed using the taken out tendon.

[Expected Results After the Surgery]

(10) The ACL is cured by a taken out tendon. Further, a cut and separated tendon may be regenerated toward a distal side (a far side of the body) after the surgery. In this case, the tendon regeneration is promoted by a guide tendon that is arranged in the same direction. Accordingly, the cut and removed tendon is expected to regenerate around the guide tendon, thus allowing the power of the tendon around the surgery site to be recovered.

The present invention provides a surgical appliance for taking out a transplant-use tendon by ablation or separation, and for assisting regeneration of the tendon at the taking out site of the tendon. By using the surgical appliance of the present invention, removal of the transplant-use tendon and regeneration of the taken out tendon at the site of taking out with a guide tendon are both performed using the same appliance.

BRIEF DESCRIPTION OF THE DRAWINGS

The instant invention will become more readily apparent from the Detailed Description of the Invention, which proceeds with reference to the drawings, in which.

DETAILED DESCRIPTION OF THE INVENTION

Figure 1:
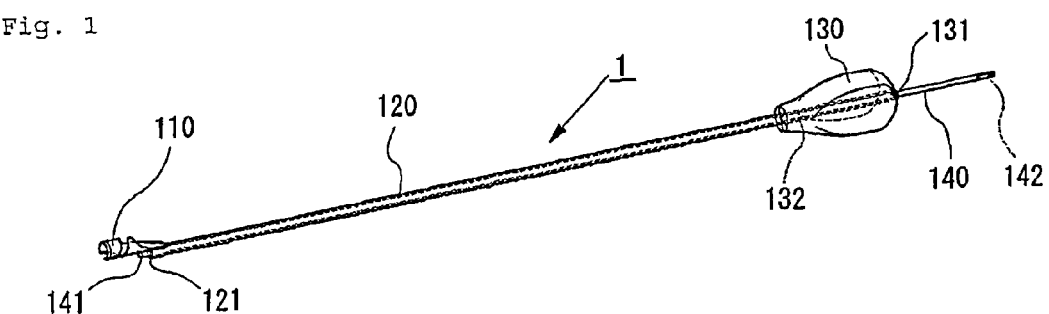
FIG. 1 is an oblique view of a surgical appliance for use in taking out a transplant use tendon and regenerating the tendon after taken out according to a first embodiment of the present invention.

Explanation of Symbols 110 tendon cutter
111 blade portion
112 a distal end side opening port
113 a proximal end side opening port
120 guide tube
121 discharge port
130 grip portion
131 insertion port
132 through hole
140 guide needle
141 (sharp conical) tip
142 threading hole
143 guide thread
210 tendon cutter
211 blade portion
212 a distal end side opening port
213 a proximal end side opening port
220 guide tube
221 discharge port
222 insertion port
230 grip portion
231 cut-off portion
250 axis body
310 tendon to be taken out
320 incision site
410 tendon cutter
412 a distal end side opening port
413 a proximal end side opening port
420 axis guide body
421 guide groove
430 grip portion
431 cut-off portion
432 guide groove of a grip portion
510 tendon cutter
511 blade portion
512 a distal end side opening port
513 a proximal end side opening port
520 guide tube
521 discharge port Preferred embodiments of the present invention will be explained in details based on drawings.

Embodiment 1

First, a surgical appliance 1 for use in taking out a transplant-use tendon and regenerating work of the tendon shown in FIG. 1 and FIG. 2 will be explained.

A surgical appliance 1 for use in taking out a transplant-use tendon and regenerating work of the tendon comprises a tendon cutter 110, a guide tube 120, a grip portion 130 and a guide needle 140.

A guide tube 120 has a predetermined length and is provided with a tendon cutter 110 at a distal end side, and a grip portion 130 at a proximal end side, respectively.

A guide needle 140 is formed in a thickness to be able to be put in and taken out and to penetrate inside of a guide tube 120.

Note that in this embodiment, the total length from a distal end of the tendon cutter 110 to a proximal end of a grip portion 130 is preferably 350 mm. However, the dimension is not limited thereto but may be variant corresponding to each surgery site.

Further, the tendon cutter 110, the guide tube 120, and the grip portion 130 may preferably be formed with aluminum alloy in a surgical appliance 1 for use in taking out a transplant-use tendon and regenerating the tendon according to this embodiment. However, the material is not limited thereto but other known materials, for example, other alloys such as a titanium alloy and stainless steel, or synthetic resins, or combination of these materials, may be used.

Figure 7:
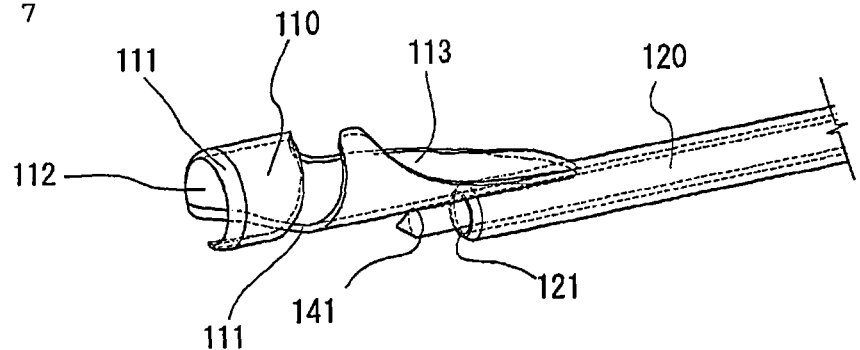
FIG. 7 is an expanded view of a tendon cutter of an open type.

The cutter 110 of this embodiment is an open-type tendon cutter shown FIG. 7. The tendon cutter 110 is preferably formed in a substantial cylindrical shape as a whole by forming a spiral shape with spaces therebetween by coiling a plate material having cutting blades. The cutting blade is disposed not only at an opening 112 at a distal end side, but at the aforementioned spaces, which comprises blade portion 111.

Note that the cutter is not limited to an open-type tendon cutter used in the present embodiment, but may alternatively be, for example, an aforementioned closed-type tendon cutter, or other known units, such as a small knife, a scalpel, or laser scalpel.

The guide tube 120 is a hollow thin tube having open opposite ends, wherein the distal end side opening port comprises the discharger port 121 of the guide needle 140, and the vicinity of the proximal end side opening port is fixed to the grip portion 130.

The grip portion 130 is provided at the proximal end side of the guide tube. A through hole 132 is formed in the grip portion 130 in the direction of the central axis and the proximal end side outlet of the through hole constitutes an insertion port 131 for a guide needle 141 (See FIG. 2).

The guide needle 140 is formed in such a length that the opposite ends 141,142 thereof may be exposed from the discharge port 121 of the guide tube and the insertion port 131 of the grip portion 130 when the guide needle is inserted into the guide tube. Note that the guide needle 140 of the present embodiment may preferably be made from aluminum alloy having flexibility or elasticity and formed with 380 mm in length and 2.7 mm in thickness.

The guide needle 140 is provided with a tip 141 that is formed in such a sharpness as to be able to break through the skin on the distal end side and a threading hole 142 on the proximal end side. Note that the tip 141 is conical in the present embodiment.

The guide needle 140 is preferably made from aluminum alloy in the present embodiment, however, the material is not limited thereto but may be other known materials, such as other metals with flexibility or elasticity and synthetic resin. Further, the guide needle is preferably formed 380 mm long and 2.7 mm thick in the present embodiment, however, the dimension is not limited thereto but can vary according to each product and usage.

Furthermore, the tip 141 is conical in the embodiment, however the shape is not limited thereto but may be other known shapes, for example, a drill-like or a blade-like shape.

(Operation)

The operation of the surgical appliance 1 for use in taking a transplant-use tendon and regenerating the tendon after take out will be explained according to FIG. 10 through FIG. 13.

Note that the order of the operation regarding B and C may be reversed in the operation described below.

[A. Taking Out Transplant-Use Tendon]

Figure 10:
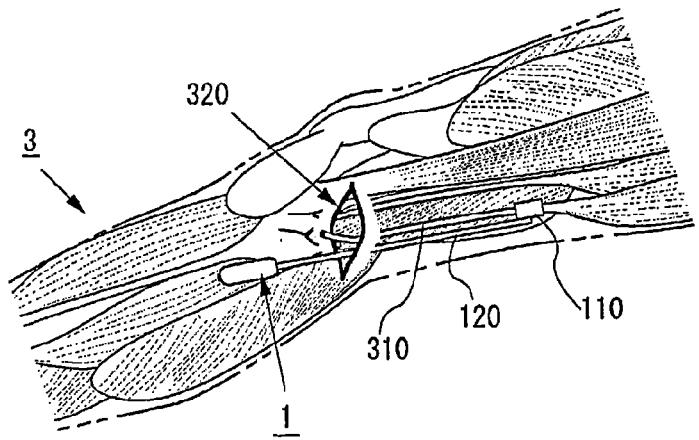
FIG. 10 is an explanatory view of a state wherein a surgical appliance for use in taking out a transplant-use tendon and regenerating the tendon after take out according to the present invention is inserted along a tendon to be taken out.
Figure 11:
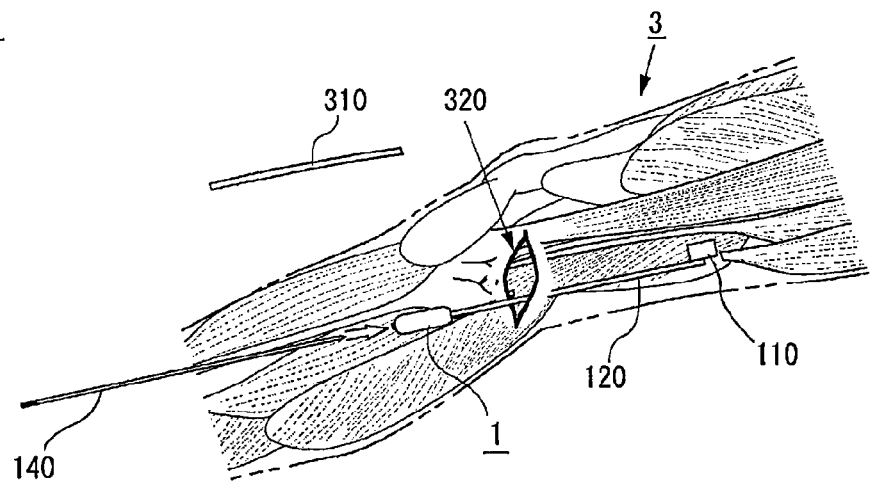
FIG. 11 is an explanatory view of a state of a surgical appliance for use in taking out a transplant-use tendon and regenerating the tendon after take out according to the present invention wherein a guide needle thereof is inserted after a tendon to be taken out is separated.

See FIG. 10 and FIG. 11.

(1) Skin inside of a knee-joint corresponding to leg part 3 is incised (hereinafter referred to as "incision site 320") and a tendon to be taken out 310, which is selected from a semitendinosus tendon, gracilis tendon, or sartorius tendon, is separated from a vicinity of the pes anserinus.

The tendon cutter 110 and the guide tube 120 of appliance 1 for cutting and separating transplant-use tendon are inserted at the incision site 320, and the guide tube 120 is inserted along the tendon to be taken out. Before this operation, the guide needle 140 is removed from the surgical appliance 1. (See FIG. 9.)

(2) An end portion of the tendon to be taken out 310 that has been separated from the pes anserinus is inserted from a distal end side opening 112 and the guide tube 120 is inserted along the tendon 310 to reach a position such that the tendon has enough length to be transplanted. The tendon 310 is then cut and separated by being pressed with a blade portion 111 disposed at the distal end of the tendon cutter 110. Alternatively, the guide tube 120 is inserted along the tendon 310 to reach a position such that the tendon has enough length to be transplanted, and then the tendon 310 is inserted in the space of the spiral portion formed at the tendon cutter 110 so as to be entangled, and is then pressed or pulled by the tendon cutter 110. Accordingly, the tendon 310 is separated with the blade portion 111 disposed between space of the spiral portion.

The separated tendon 310 is removed by pulling the tendon out from the inside of the body. Note that, at this point, the guide tube 120 of the surgical appliance 1 remains inside of the body. (See FIG. 10.)

[B. Regenerating Work at the Site of a Transplant-Use Tendon that has been Taken Out]

Figure 12:
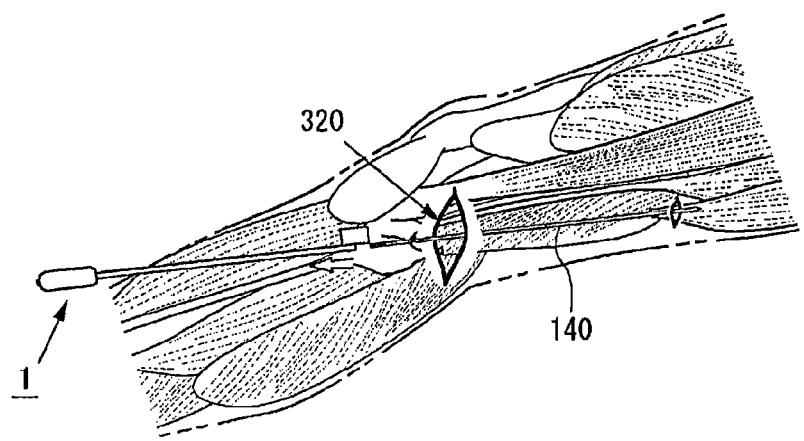
FIG. 12 is an explanatory view of a state of a surgical appliance for use in taking out a transplant-use tendon and regenerating the tendon after take out according to the present invention wherein a tendon cutter and a guide tube thereof are pulled out from the inside of the body and a guide needle thereof is arranged corresponding to a direction of a taken out tendon.
Figure 13:
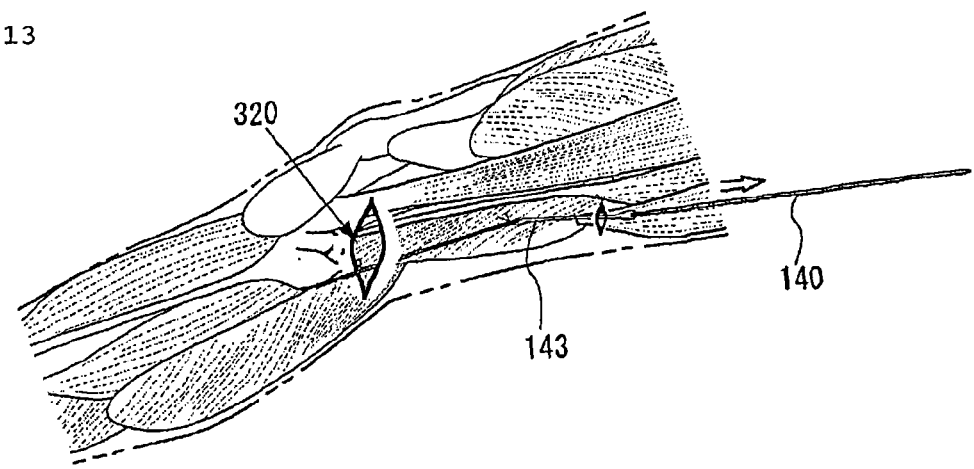
FIG. 13 is an explanatory view of a state of a surgical appliance for use in taking out a transplant-use tendon and regenerating the tendon after take out according to the present invention wherein a guide needle thereof is pulled out from the inside of the body and a guide thread thereof is arranged corresponding to a direction of a taken out tendon.

See FIG. 12 and FIG. 13.

(3) A guide tendon is prepared. Specifically, among the tendons 310 described above, parts of the tendons of tendons other than the removed tendon are cut and separated in a longitudinal direction at the tendon body between an origin of the tendon, which is at an inguinal region, and an insertion of the tendon, which is a vicinity of the pes anserinus, and are pulled out from the incision site 320.

(4) The guide needle 140 is inserted into the inside of the guide tube 120 from the inserting port 131, and the skin is penetrated with the tip 141 disposed at the distal end of the guide needle 140 at the position at which the removed tendon is cut and separated, which is an inner side of vicinity where the removed tendon is separated. (See FIG. 12)

(5) A part of the guide needle 140 which is protruded from the skin is gripped, and the guide tube 120 is pulled out from the incision site 320 of the body. (See FIG. 12)

(6) A guide thread 143 is put through a threading hole 142 of the guide needle 140, and the thread is looped. Note that the guide thread 143 may be put through the threading hole 142 and looped beforehand.

(7) The guide needle 140 is pulled out from the cut that was cut with the tip 141 during the procedure (4) and the guide thread 143 is arranged corresponding to the direction and the position of the taken out tendon. Thus, the guide thread 143 for leading a guide tendon is able to be in a direction and position of the tendon 310 direction before the direction and position of the guide tendon is arranged to correspond to the direction and position of the taken out tendon.

(8) The cut end of the guide tendon that has been pulled out is put into a loop of the guide thread and connected with the thread 143 and then pulled with thread toward the proximal side, a nearer side to the body trunk. By doing this, the guide tendon is able to be arranged to correspond to the direction and position of the taken out tendon (FIG. 13) so that an operation in which the guide tendon is guided to the pes anserinus by moving and arranging the guide tendon to the direction and position of a taken out tendon, which procedure was difficult in conventional surgical procedures, can be performed easily using the instant invention. Further, guided by the transferred tendon, a new tendon to be regenerated is allowed to attach properly to the pes anserinus which is a tendonious insertion before taken out and so there is a higher possibility that a tendon will be regenerated. Accordingly, the muscle with tendon power can be expected to be recovered to the level before the surgery.

[C. Curing of ACL]

(9) ACL curing work is performed using the taken out tendon 310.

[Expected Results After the Surgery]

(10) The ACL is cured by a taken out tendon 310. Further, a separated tendon from taken out tendon may be regenerated toward distal (a farther side from the body) after the surgery. In the case of the present invention, the tendon regenerating is promoted by a guide tendon that is arranged in the same position and direction. Accordingly, the taken out tendon part is expected to be regenerated allowing the power of tendon around the surgery site to be recovered.

Embodiment 2

The second embodiment of the present invention will be explained in detail according to drawings. Note that explanation of the same or similar parts as described in reference to the first embodiment will be omitted to avoid unnecessary duplication.

Figure 3:
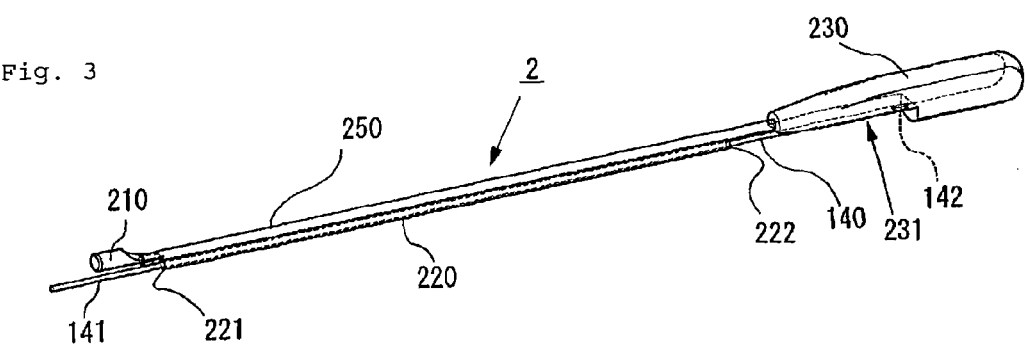
FIG. 3 is an oblique view of the surgical appliance for use in taking out a transplant-use tendon and regenerating the tendon after take out according to another embodiment of the present invention.
Figure 4:
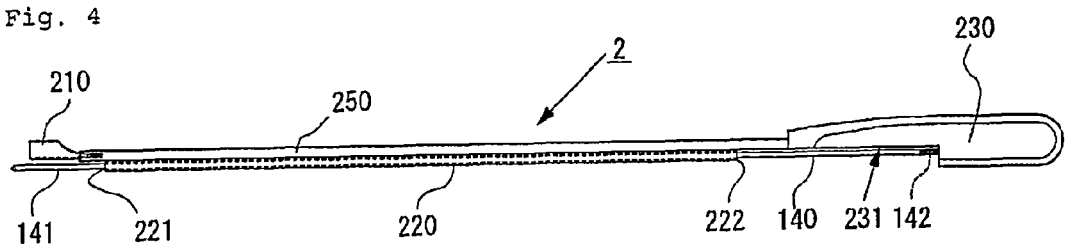
FIG. 4 is a side view of the surgical appliance according to the embodiment of FIG. 3.

A surgical appliance 2 for use in taking out a transplant-use tendon and regenerating the tendon as shown in FIG. 3 and FIG. 4 will be explained.

The surgical appliance 2 for use in taking out a transplant-use tendon and regenerating the tendon comprises a tendon cutter 210, a guide tube 220, a grip portion 230, a solid-core axis body 250 and a guide needle 140. Note that because the guide needle 140 is the same as the aforementioned guide needle 140, the explanation will be omitted.

Further, in the present embodiment, the total length from the distal end of the tendon cutter 210 to the proximal end of the grip portion 230 is preferably 400 mm, however, the dimension is not limited thereto but may be variant corresponding to each surgery site.

The axis body 250 has a predetermined length and is provided with a tendon cutter 210 at a distal end side and a grip portion 230 at a proximal end side, respectively.

Figure 8:
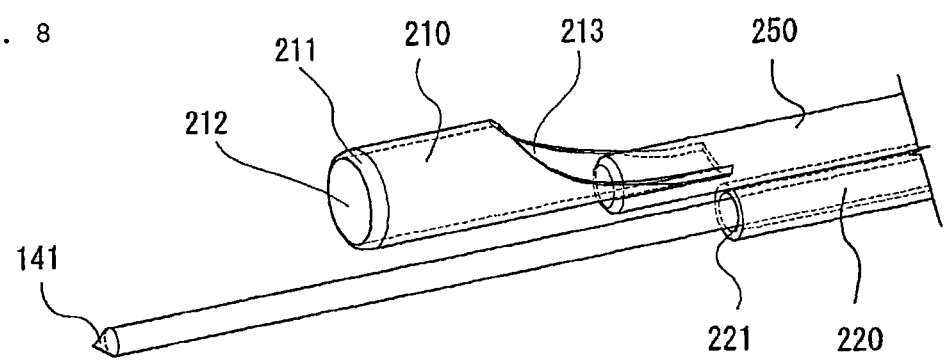
FIG. 8 is an expanded view of a tendon cutter of a closed type.

In the present embodiment, the tendon cutter 210 is a closed-type cutter as shown in FIG. 8. The tendon cutter 210 is formed in a cylindrical shape and has openings at the distal end side and the proximal end side. The opening at the distal end side comprises a distal end side opening 212 wherein a blade portion 211 is formed at a peripheral portion thereof. The blade portion 211 is formed so as to be able to cut and separate tendon by pressing.

Note that in the present embodiment a closed-type cutter is preferably used, however the tendon cutter is not limited thereto, but the aforementioned open-type tendon cutter or other known units, such as a small knife including scalpels, or laser scalpel, may alternatively be used.

The grip potion 230 is formed in a substantial spindle shape, and is provided with a cut-off portion 231 which is formed by cutting off a part of the grip portion in a direction from the distal end to the substantial central portion. (See FIG. 3 and FIG. 4)

The guide tube 220 is a hollow thin tube having open opposite ends, shorter than the axis body 250 to a certain degree, and bonded in a longitudinal direction of the axis body 250.

The guide tube 220 has an inner diameter formed such that the guide needle 140 is able to be taken in and out and penetrate inside thereof, wherein a distal end side opening comprises a discharge port 221 for the guide needle 140 while a proximal end side opening comprises a inserting port 222 for the guide needle 140.

(Operation)

Note that other than the operation in the process (2) of [A. taking out of transplant-use tendon] wherein; an end of a tendon to be taken out 310 which has been separated from the pes anserinus is inserted in a distal end side opening 112 of a tendon cutter 110 and inserted along the tendon to be taken out 310 to reach a position which has enough length for transplantation and the tendon to be taken out 310 is separated by being pressed with a blade portion 111 disposed at the distal end of the tendon cutter 110, the operation of the surgical appliance 2 for use in taking out a transplant-use tendon and regenerating work of the tendon is the same as that of a surgical appliance 1 for use in taking out a transplant-use tendon and regenerating work of the tendon, explanation will be omitted.

Embodiment 3

The mode of the embodiment 3 of the present invention will be explained in details corresponding to drawings. Note that explanation of the same or similar parts as described in reference to the other embodiments will be omitted to avoid unnecessary duplication.

A surgical appliance 4 for use in taking out a transplant-use tendon and regenerating work of the tendon shown in FIG. 5 and FIG. 6 will be explained.

The surgical appliance 4 for use in taking out a transplant-use tendon and regenerating work of the tendon comprises a tendon cutter 410, a guide axis body 420, a grip portion 430 and guide needle 140. Note that because the guide needle 140 is the same as the aforementioned guide needle 140, the explanation will be omitted. Further, because the tendon cutter 410 has a similar constitution to the tendon cutter 210 shown in FIG. 8, the explanation will be omitted.

Furthermore, in the present embodiment, the total length from the distal end of the tendon cutter 410 to the proximal end of the grip portion 430 is approximately 400 mm, however, the dimension is not limited thereto but may be variant corresponding to each surgery site.

The tendon cutter 410 and the grip portion 430 are provided at opposite ends of the guide axis body 420, respectively.

A connecting portion of the tendon cutter 410 and the guide axis body 420 is disposed so as to allow the guide needle 140 to protrude from an end of the tendon cutter. (See FIG. 5 and FIG. 6.)

Note that in the present embodiment, a closed-type tendon cutter (See FIG. 8) is used. However, the tendon cutter is not limited thereto but other known units, such as the aforementioned open-type tendon cutter may alternatively be used. (See FIG. 7)

A guide axis body 420 is formed with a guide groove 421 with predetermined depth and width in a direction to the center of the axis body.

The guide groove 421 is formed in a longitudinal direction of the guide axis body 420 and is configured such that the guide needle 140 that is mated therewith is able slide along the guide groove 421. Note that in the present embodiment, the guide groove 421 is formed longitudinally extending in the entire length, however, it is not limited to this mode but may be formed, for example, in any length in the longitudinal direction of the axis body as long as it is capable of guiding the guide needle 140.

The grip portion 230 is substantially spindle-shaped and is provided with a cut-off portion 431 which is formed by cutting off a part thereof from a distal end to the substantially central part. (See FIG. 5 and FIG. 6)

Note that in the present embodiment, the guide groove of a grip portion 432 is formed in a longitudinal direction of the cut-off portion 431 and on the extension of the straight line of the guide groove 421 formed at the guide axis body 420, however, the mode is not limited thereof but may alternatively be formed without the guide groove.

(Operation)

(1) When a guide needle 140 is used for the surgical appliance 4 for use in taking out a transplant-use tendon and regenerating the tendon, the surgical appliance 4 is used in a way in which the guide needle 140 is not inserted into a tube body but the guide needle is moved (or slid) along the guide grove 421.

(2) Further, in the surgical appliance 4 for use in taking out a transplant-use tendon and regenerating work of the tendon, the guide needle 140 which is passed through the guide groove 421, is passed through toward the distal end side opening 412 of the tendon cutter 410 from the proximal end side opening 413 of the tendon cutter, and is protruded.

Note that since the portions of the operation described other than in (1) and (2) is similar to that of the surgical appliance 1 for use in taking out a transplant-use tendon and regenerating work of the tendon, the explanation will be omitted.

Embodiment 4

The mode of the forth embodiment will be explained in details corresponding to drawings. Note that explanation of the same or similar parts as described in reference to the other embodiments will be omitted to avoid unnecessary duplication.

Figure 9:
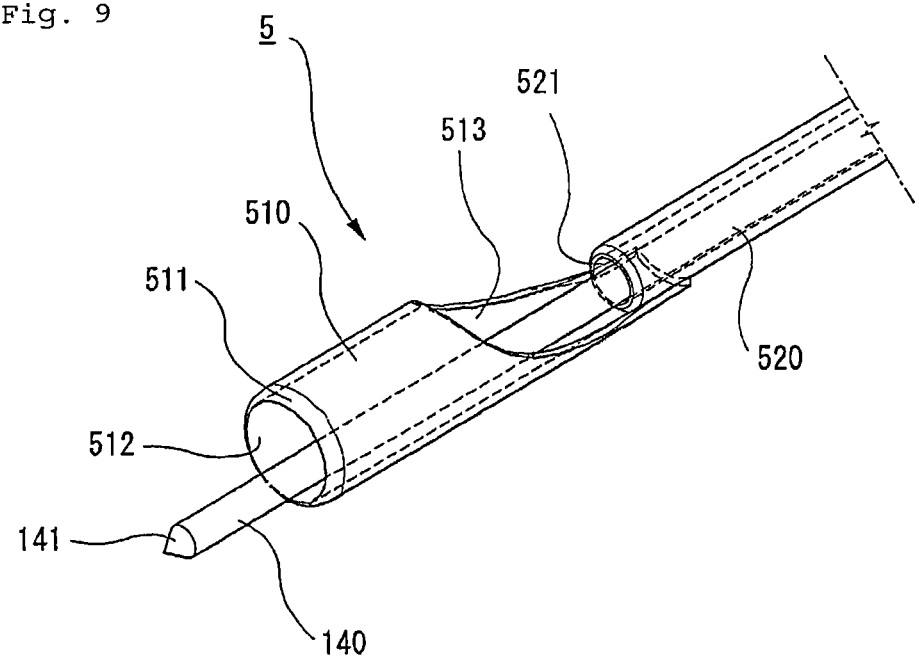
FIG. 9 is an expanded view of an end part of a surgical appliance for use in taking out a transplant-use tendon and regenerating the tendon after take out according to another embodiment of the present invention.

A surgical appliance 5 for use in taking out a transplant-use tendon and regenerating work of the tendon shown in FIG. 9 will be explained.

The surgical appliance 5 for use in taking out a transplant-use tendon and regenerating work of the tendon comprises a tendon cutter 510, a guide tube 520, a grip portion (not shown in drawings) and a guide needle 140.

Note that the surgical appliance 5 for use in taking out a transplant-use tendon and regenerating work of the tendon has a similar configuration to that of the surgical appliance 1. The difference can be described as follows.

(1) In the surgical appliance 5, a closed-type tendon cutter is used as a tendon cutter 510. (See FIG. 8)

(2) The tendon cutter 510 and a guide tube 520 are provided along the same longitudinal axis and a guide needle 140 that has been penetrated/passed through the guide tube 520 is arranged so as to protrude from a distal end side of the tendon cutter 510. (See FIG. 9.)

Figure 2:
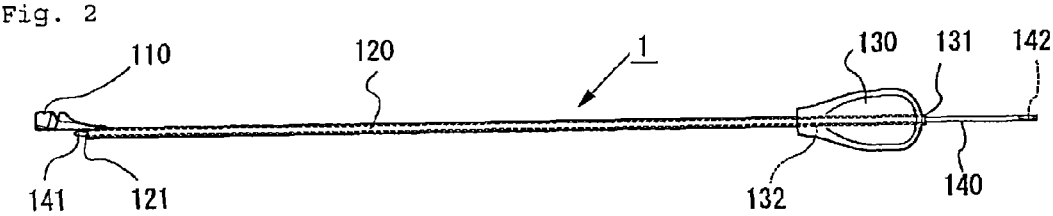
FIG. 2 is a side view of the surgical appliance according to the first embodiment.
Figure 5:
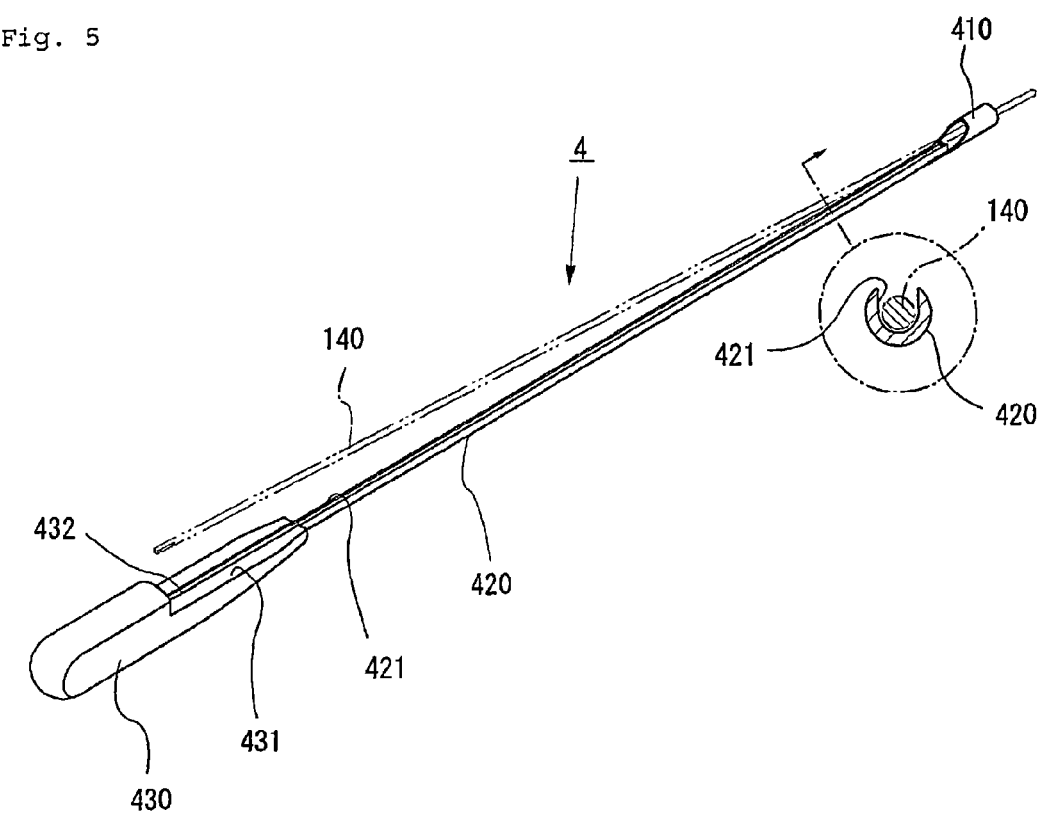
FIG. 5 is an explanatory oblique view including a cross-sectional view of a part of the surgical appliance for use in taking out a transplant-use tendon and regenerating the tendon after take out according to another embodiment of the present invention.
Figure 6:
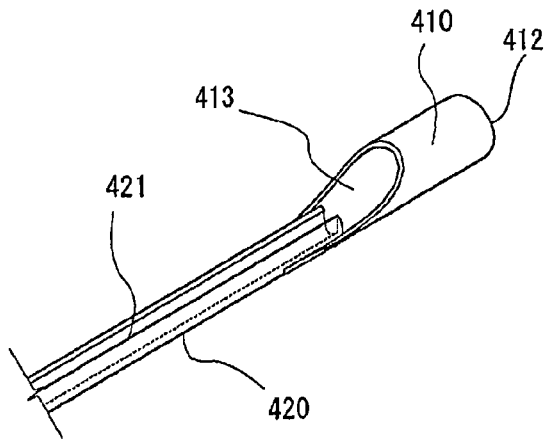
FIG. 6 is an expanded view of an end part of the surgical appliance according to the embodiment of FIG. 5.

The same grip portion as the grip portion 130 shown in FIG. 1 is preferably used, however, it is not limited to that of the FIG. 1; the grip portion 430 shown in FIG. 5 may also be used.

Because a guide needle 140 used in the present embodiment is the same as that described above, the explanation will be omitted.

Note that in the surgical appliance 5, a closed-type tendon cutter (See FIG. 8.) is used as a tendon cutter 510, however, the tendon cutter is not limited thereto but other known units such as the aforementioned open-type tendon cutter (See FIG. 7) may be used.

Further, in the present embodiment, the total length from a distal end of a tendon cutter 110 to proximal end of a grip portion 130 is preferably 350 mm, however, the dimension is not limited to but may be variant corresponding to each surgery site.

(Operation)

In the surgical appliance [[4]]5 for use in taking out a transplant-use tendon and reconstructing the tendon, a guide needle 140 that comes out from a discharge port 521 of a guide tube 520 passes through from a proximal end side opening 513 to a distal end side opening 512. Except for the above operation, the explanation is the same as that described in the aforementioned portions of the operation of the surgical appliance 1, the further explanation will be omitted.

The terms and expressions used in the present specification and the scope of claims are merely for the sake of the explanation made herein, and the present invention is not limited thereto. Those skilled in the art will readily recognize additional numerous adaptations and modifications which can be made to the present invention which fall within the scope of the invention as claimed in the claims. Moreover, it is intended that the scope of the present invention include all foreseeable equivalents to the structures as described with reference to the drawings. Accordingly, the invention is to be limited only by the scope of the claims and their equivalents.

The present invention provides a surgical appliance for taking out a transplant-use tendon by ablation or separation and assisting regeneration of the tendon at the taking out site of the tendon. By using the surgical appliance of the present invention, tendon taking out work and regeneration work for the taken-out tendon at the site of taking out can both be performed with the same one appliance.

What is claimed is:

1. A surgical appliance for taking out a transplant-use tendon and for assisting regeneration of the tendon after take out of the tendon, the surgical appliance configured to be inserted into the inside of a living body to be operated on, and comprising:
 a tendon-cutting and separating unit;
 a hollow tube having open opposing ends; and
 a needle-like body configured to be inserted in and to penetrate through the tube, wherein
 the tendon-cutting and separating unit is provided at a distal end side of the tube;
 an opening portion at the distal end side of the tube comprises a discharging port while an opening portion at the proximal end side of the tube comprises an inserting port for inserting the needle-like body; and
 the needle-like body is provided, with a skin-breaking portion for breaking the skin and is provided with a threading hole at the proximal end side thereof.

2. The surgical appliance according to claim 1, wherein;
the needle-like body is configured to be in a state of being inserted in the tube and has a length such that the end portion of the needle-like body is exposed from one or both opening portions of the tube.

3. The surgical appliance according to claim 1, wherein:
a grip portion is provided at the proximal end side of the tube.

\* \* \* \* \*